(12) United States Patent
Er et al.

(10) Patent No.: US 7,333,856 B1
(45) Date of Patent: Feb. 19, 2008

(54) METHOD AND SYSTEM TO GRAPHICALLY DISPLAY PROGRAMMING PARAMETERS FOR MULTI-CHAMBER DEVICES

(75) Inventors: Siew Bee Er, Fair Oaks Ranch, CA (US); Qiuju Huang, Northridge, CA (US); Euljoon Park, Valencia, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 516 days.

(21) Appl. No.: 10/847,709

(22) Filed: May 17, 2004

(51) Int. Cl.
*A61N 1/362* (2006.01)

(52) U.S. Cl. .......................................... 607/30; 607/27

(58) Field of Classification Search ................. 607/27, 607/30, 32, 59, 60, 62, 31, 46
See application file for complete search history.

(56) References Cited

U.S. PATENT DOCUMENTS

| | | | |
|---|---|---|---|
| 4,809,697 A * | 3/1989 | Causey et al. ................. 607/31 |
| 5,902,324 A | 5/1999 | Thompson et al. ............. 607/9 |
| 6,070,101 A | 5/2000 | Struble et al. ................. 607/9 |
| 6,081,748 A | 6/2000 | Struble et al. ................. 607/9 |
| 6,122,545 A | 9/2000 | Struble et al. ................. 607/9 |
| 6,438,408 B1 | 8/2002 | Mulligan et al. ............ 600/510 |
| 6,456,878 B1 | 9/2002 | Yerich et al. ................... 607/9 |
| 2002/0077669 A1 | 6/2002 | Lindh et al. ................... 607/27 |
| 2002/0077859 A1 | 6/2002 | Stahmann et al. .............. 705/3 |
| 2002/0115939 A1 | 8/2002 | Mulligan et al. ........... 600/510 |
| 2003/0176899 A1* | 9/2003 | Samuelsson et al. ......... 607/60 |
| 2004/0111131 A1* | 6/2004 | Hu et al. ....................... 607/60 |
| 2005/0177206 A1* | 8/2005 | North et al. .................. 607/60 |

FOREIGN PATENT DOCUMENTS

| | | |
|---|---|---|
| WO | WO 99/55415 | 4/1999 |
| WO | WO 01/36042 A1 | 5/2001 |
| WO | WO 01/08748 A1 | 8/2001 |

* cited by examiner

*Primary Examiner*—Scott M. Getzow

(57) ABSTRACT

A method and system for programming an implantable therapeutic stimulation device sensing from and delivering therapeutic stimulations to multiple sites within a patient under a plurality of programmable parameters. The method includes automatically determining which parameters need to be programmed, graphically indicating specific parameters that need to be programmed in a spatial correspondence to the affected sites in the patient and/or displaying a waveform corresponding to expected physiological activity with the programming, and providing control inputs to program the specific parameters. The method can also include automatically evaluating the programmed parameters, and if errors exist in the programming, indicating the errors and awaiting corrective input, else programming the implantable device. The method can also include automatically determining a number of sensing and stimulation electrodes connected to the device.

25 Claims, 8 Drawing Sheets

○ = FIXED POINT

☐ = POINT MOVABLE ALONG THE TIME AXIS

OUTPUT TO RA LEAD
VOLTAGE, PULSE DURATION
RA SENSITIVITY
PVARP FOR RIGHT ATRIAL LEAD
OUTPUT POLARITY
SENSING POLARITY

THIS SECTION RELATES RA AND LA
$A_RA_L$ = DEFAULT IS 0 MS, + IS R BEFORE L, – IS L BEFORE R (UNITS IN MILLISECONDS)
$P_RA_L$ = COUPLING INTERVAL IF SENSE IN RA FIRST
$P_LA_R$ = COUPLING INTERVAL IF SENSE IN LA FIRST

OUTPUT TO LA LEAD
VOLTAGE, PULSE DURATION
LA SENSITIVITY
PVARP FOR LEFT ATRIAL LEAD
OUTPUT POLARITY
SENSING POLARITY $A_R/P_R$ $A_L/P_L$

PROGRAMMED PARAMETERS

BASIC PARAMETERS

| Parameter | INITIAL | PRESENT | Units |
|---|---|---|---|
| MODE | DDD | DDD | |
| BASE RATE | 60 | 60 | ppm |
| HYSTERESIS RATE | OFF | OFF | ppm |
| REST RATE | OFF | OFF | ppm |
| MAX TRACK RATE | 150 | 150 | ppm |
| 2:1 BLOCK RATE | 160 | 160 | ppm |
| AV DELAY | 180 | 180 | ms |
| PV DELAY | 150 | 150 | ms |
| RATE RESP. AV/PV DELAY | OFF | OFF | |
| SHORTEST AV/PV DELAY | 70 | 70 | ms |
| VENTRICULAR REFRACTORY | 200 | 200 | ms |
| ATRIAL REFRACTORY (PVARP) | 225 | 225 | ms |
| VENTRICULER: | | | |
| V. AUTOCAPTURE | OFF | OFF | |
| V. PULSE AMPLITUDE | 4.00 | 4.00 | V |
| V. PULSE WIDTH | 0.6 | 0.6 | ms |
| V. SENSITIVITY | 12.5 | 12.5 | mV |
| V. PULSE CONFIGURATION | BIPOLAR | BIPOLAR | |
| V. SENSE CONFIGURATION | BIPOLAR | BIPOLAR | |
| ATRIAL: | | | |
| A. PULSE AMPLITUDE | 4.00 | 4.00 | V |
| A. PULSE WIDTH | 0.6 | 0.6 | ms |
| A. SENSITIVITY | 0.5 | 0.5 | mV |
| A. PULSE CONFIGURATION | BIPOLAR | BIPOLAR | |
| A. SENSE CONFIGURATION | BIPOLAR | BIPOLAR | |
| MAGNET RESPONSE | BATTERY TEST | BATTERY TEST | |

EXTENDED PARAMETERS

| Parameter | INITIAL | PRESENT | Units |
|---|---|---|---|
| AUTOINTRINSIC CONDUCTION SEARCH | OFF | OFF | |
| NEGATIVE AV/PV HYSTERESIS/SEARCH | OFF | OFF | |
| AUTO MODE SWITCH | DDI | DDI | |
| ATRIAL TACHYCARDIA DETECTION RATE | 170 | 170 | ppm |
| AMS BASE RATE | 60 | 60 | ppm |
| POST VENT. ATRIAL BLANKING (PVAB) | 100 | 100 | ms |
| VENT. SAFETY STANDBY | ON | ON | |
| VENT. BLANKING | 12 | 12 | ms |
| PVC OPTIONS | +PVARP ON PVC | +PVARP ON PVC | |
| PMT OPTIONS | AUTO DETECT | AUTO DETECT | |
| PMT DETECTION RATE | 120 | 120 | bpm |

SENSOR PARAMETERS

| Parameter | INITIAL | PRESENT |
|---|---|---|
| SENSOR | PASSIVE | PASSIVE |
| MAX SENSOR RATE | 130 | 130 ppm |
| THRESHOLD | AUTO(+0.0) | AUTO(+0.0) |
| MEAS. AVERAGE SENSOR | 2.6 | 2.6 |
| SLOPE | AUTO(+2) | AUTO(+2) |
| MEASURED AUTO SLOPE | 11 | 11 |
| REACTION TIME | FAST | FAST |
| RECOVERY TIME | MEDIUM | MEDIUM |

METHOD AND SYSTEM TO GRAPHICALLY DISPLAY PROGRAMMING PARAMETERS FOR MULTI-CHAMBER DEVICES

FIELD OF THE INVENTION

The invention is related to the field of implantable medical devices and, in particular, to an improved user-friendly method of programming device parameters and displaying the programmed values in a graphical manner.

DESCRIPTION OF THE RELATED ART

Implantable stimulation devices provide automatic monitoring and delivery of therapeutic stimulation for a variety of medical conditions. The implantable stimulation device typically monitors a variety of physiological parameters and in many applications this occurs via a plurality of sense electrodes. The implantable stimulation device also typically includes an implantable pulse generator to generate appropriate stimulation pulses and a programmable microprocessor to evaluate the monitored physiological parameters, determine when therapeutic stimulation is indicated, and to selectively induce the implantable pulse generator to generate these stimulation pulses. The therapeutic stimulations are typically provided via a plurality of stimulation electrodes and the sensing and stimulation electrodes are typically provided on one or more implantable leads.

One particular example of an implantable stimulation device is an implantable cardiac stimulation device such as a pacemaker and/or implantable cardioverter-defibrillator (ICD). Implantable cardiac stimulation devices have become increasingly sophisticated and complicated and it is now possible for implantable cardiac stimulation devices to sense and/or provide therapeutic stimulation at all four chambers of the heart, i.e. both left and right ventricles and atria.

Sensed physiological signals, such as cardiac depolarizations in the various chambers of the heart, are sensed via a plurality of sense electrodes which provide signals corresponding to the depolarization signals to the implantable cardiac stimulation device and the microcontroller thereof. The microcontroller evaluates these sensed signals and "detects" whether the sensed signals indicate acceptable cardiac activity or a physiological anomaly indicative of a cardiac arrhythmia. Upon detection of a cardiac arrhythmia, the microcontroller of the implantable cardiac stimulation device is adapted to induce the implantable pulse generator to generate an appropriate stimulation pulse(s) which is then delivered via one or more stimulation electrodes to the appropriate location(s) in the patient's heart.

This detection of cardiac arrhythmia and consequent delivery of stimulation pulses occurs according to programmed algorithms which makes detection and stimulation delivery decisions based on a number of programmable decision parameters which, in modern implantable stimulation devices, can exceed several dozen different parameters. These parameters are determinate in whether a sensed signal is determined as a "detected" cardiac arrhythmia and also for establishing the amplitude and duration of an indicated therapeutic stimulation pulse or pulse train. Certain individual parameters are also interrelated to one another such that a change in one parameter affects the function of another parameter in the decision algorithms.

Due to the wide variety of implantable stimulation devices available from different manufacturers, the plurality of sense/stimulation electrodes that may or may not be connected in an individual case, and the individual characteristics of any particular patient and their pathology, these individual parameters are preferably at least partially individually programmed for a particular patient who is provided with a particular version of an implantable stimulation device. This individualized programming is typically performed based on a variety of characteristics of the implantable device, leads (which include the electrodes), evaluations of the specific physiological condition of the patient, and the attending clinician's professional training and judgement.

The implantable stimulation device is typically programmed at the time of the implantation procedure following attachment to the implanted leads and closure of the surgical incision. Further, as the patient's condition is generally not static over time, improvements to the evaluation and treatment algorithms may become available, a patient's medication regimen may change, and/or other changes may occur over time indicating a change in device programming, it is highly desirable to be able to program or to adjust the functional parameters of the devices without requiring invasive procedures. Thus, implantable stimulation devices are typically provided with a telemetry link such that an external device may telemetrically communicate with the implanted device so as to provide programming control inputs to the implantable device without physically accessing the device. This is typically done with the use of a programmer which provides the ability for a user to telemetrically communicate with the implantable device and the programmer typically includes display capability and user inputs to allow the user to view information and provide control inputs.

The programmer typically portrays the current and/or proposed programmed parameters in an alpha-numeric format arranged in lists or groups on one or more user screens, e.g. "basic parameters", "extended parameters", and "sensor parameters". Attending clinical personnel, such as physicians, are typically very familiar with the patient's physiological parameters and individual pathologies and understand the desired physiological output of, for example, the heart. Other attending clinical personnel, such as clinical engineers and sales representatives for the implantable stimulation devices and the programmers, are typically quite familiar with the available programmable parameters and the protocol for programming these parameters in particular devices and with particular programmers.

However, presentation of these relatively large number of programmable parameters in lists in an alpha-numeric format is not particularly intuitive and does not typically provide a readily understood interrelationship between related parameters and how a change in one parameter may affect others. There is also a significant burden on the clinicians to learn and program each of these parameters, particularly in the increasing number for devices sensing and stimulating to multiple chambers. Thus, learning the large number of individual parameters, appropriate settings therefor, and how particular settings would be expected to affect the sensing and therapy delivery of the device requires a large degree of skill and training and is complex and time-consuming in execution.

Thus, it will be appreciated that there is a need for presenting information related to programming of implantable stimulation devices in a manner that is more intuitive and allows attending clinical personnel to more readily and fully understand and manipulate the programming parameters to more efficiently program a device for the specific needs of an individual patient. There is also a need for a system and method of programming implantable stimulation devices that reduces the burden on attending clinical personnel to learn specific programming protocols for different programmers and/or implantable devices.

SUMMARY

The aforementioned needs are satisfied by a method of programming an implantable therapeutic stimulation device sensing from and delivering therapeutic stimulations to multiple sites within a patient under a plurality of individually programmable parameters, the method comprising displaying a waveform indicating expected physiological activity under a first set of programmed parameters of the device, automatically determining which of the parameters need to be individually programmed, indicating the parameters that need to be programmed via indicating regions of the displayed waveform that are affected by the indicated parameter, providing control inputs to reprogram the indicated parameters, and indicating as indicated parameters are reprogrammed by modifying the waveform in accordance with the reprogrammed parameters.

In one embodiment, providing control inputs to reprogram the indicated parameters comprises temporarily programming the parameters and further comprises automatically evaluating the temporarily programmed parameters entered and if errors exist in the temporary programming, indicating the errors and awaiting corrective input, else programming the implantable device with the temporary programming.

Providing control inputs to reprogram the indicated parameters can comprise manipulating a corresponding region of the displayed waveform and herein displaying the waveform can comprise displaying the waveform as a graphical user interface and manipulating the corresponding region of the waveform can comprise selecting and dragging the corresponding region of the waveform.

In one embodiment, providing control inputs comprises selecting a numerical parameter value. Selecting a numerical parameter value can comprise incrementing or decrementing the parameter.

In one embodiment, providing control inputs to reprogram certain of the indicated parameters that affect other programmable parameters automatically prompts for reprogramming the other affected parameters. The programmed parameters can comprise AV delay. One embodiment further comprises automatically determining which of a plurality of sensing and stimulation electrodes are connected to the device.

Another embodiment is a method of programming an implantable therapeutic stimulation device sensing from and delivering therapeutic stimulations to multiple sites within a patient under a plurality of individually programmable parameters, the method comprising automatically determining which parameters need to be individually programmed, graphically displaying the parameters that need to be programmed such that the parameters are respectively displayed in a spatial relationship corresponding to a spatial relationship of the sites within the patient expected to be affected by the parameters, providing control inputs to program the parameters, and indicating as parameters are programmed.

In one embodiment, providing control inputs temporarily programs the parameters and further comprises automatically evaluating the temporarily programmed parameters and, if errors exist in the temporary programming, indicating the errors and awaiting corrective input, else programming the implantable device with the temporary programming. In one embodiment, evaluating the temporarily programmed parameters occurs once all of the needed programming is entered.

One embodiment further comprises displaying a waveform indicating expected physiological activity under a current set of the programmed parameters and/or automatically determining a number of sensing and stimulation electrodes connected to the device. In one embodiment the programmable parameters comprise anterograde or retrograde conduction between two cardiac chambers.

Another embodiment is a physicians programmer for telemetrically communicating with an implantable stimulation device so as to transceive data and commands therewith wherein the programmer displays a waveform corresponding to expected physiological activity of a patient provided with the device as programmed with a first set of programming, indicates portions of the waveform corresponding to specific programmable operational parameters of the device that need to be individually programmed for the patient, receives control inputs from a user to program the indicated parameters, modifies the displayed waveform in accordance with the control inputs, and provides commands to the device to program the device in accordance with the control inputs.

In one embodiment, the programmer modifies the displayed waveform, upon receipt of the control input for one programmable parameter, in accordance with other programmable parameters that are interrelated with the one programmable parameter and/or automatically evaluates the control inputs and indicates any errors in programming.

In one embodiment, the displayed waveform comprises a waveform corresponding to the expected cardiac activity of the patient. In one embodiment, the programmer indicates portions of the waveform corresponding to specific programmable operational parameters by indicating the portions of the waveform with a specific icon. In one embodiment, the programmer automatically determines a number of sensing and stimulation electrodes connected to the implantable device.

A further embodiment is a physicians programmer for telemetrically communicating with an implantable stimulation device so as to transceive data and commands therewith wherein the programmer automatically determines which parameters need to be individually programmed, graphically displays the parameters that need to be programmed such that the parameters are respectively displayed in a spatial relationship corresponding to a spatial relationship of sites within the patient expected to be affected by the parameters, receives control inputs from a user to program the indicated parameters, and provides commands to the device to program the device in accordance with the control inputs.

In one embodiment, the programmer receives the control inputs, temporarily programs the parameters, automatically evaluates the temporarily programmed parameters and, if errors exist in the temporary programming, indicates the errors and awaits corrective input, else programs the implantable device with the temporary programming and the programmer can evaluate the temporarily programmed parameters before or after all of the needed programming is entered.

In one embodiment, the programmer displays a waveform indicating expected physiological activity under a current set of programmed parameters. In one embodiment, the programmable parameters comprise anterograde or retrograde conduction between two cardiac chambers. In one embodiment, the programmer automatically determines a number of sensing and stimulation electrodes connected to the device.

The invention provides methods and devices to efficiently view the expected effect of a plurality of programmable parameters of the implantable device in a similar manner to a commonly understood and used standard clinical tool, e.g. a graphically displayed IEGM/ECG. The invention allows attending clinical personnel to directly manipulate the standard graphical display to a desired configuration without learning different protocols, terminology, sequences, etc. that may apply to a specific device. The invention also provides the added convenience of automatically indicating how changes in certain parameters would affect other related parameters and also the ability to automatically self-check a set of programming for possible errors and indicate any errors for correction. These and other objects and advantages of the invention will be more apparent from the following description taken in conjunction with the accompanying drawings.

BRIEF DESCRIPTION OF THE DRAWINGS

FIG. 7 is a detail of a sample screen shot following user selection of the P-wave on the schematic ECG of FIG. 6;

FIGS. 8A-8D show details of the schematic ECG waveform for several different programmed parameters; and FIG. 9 is a list of one embodiment of a set of programmable parameters and their initial and present settings for one particular device configuration and for one patient.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
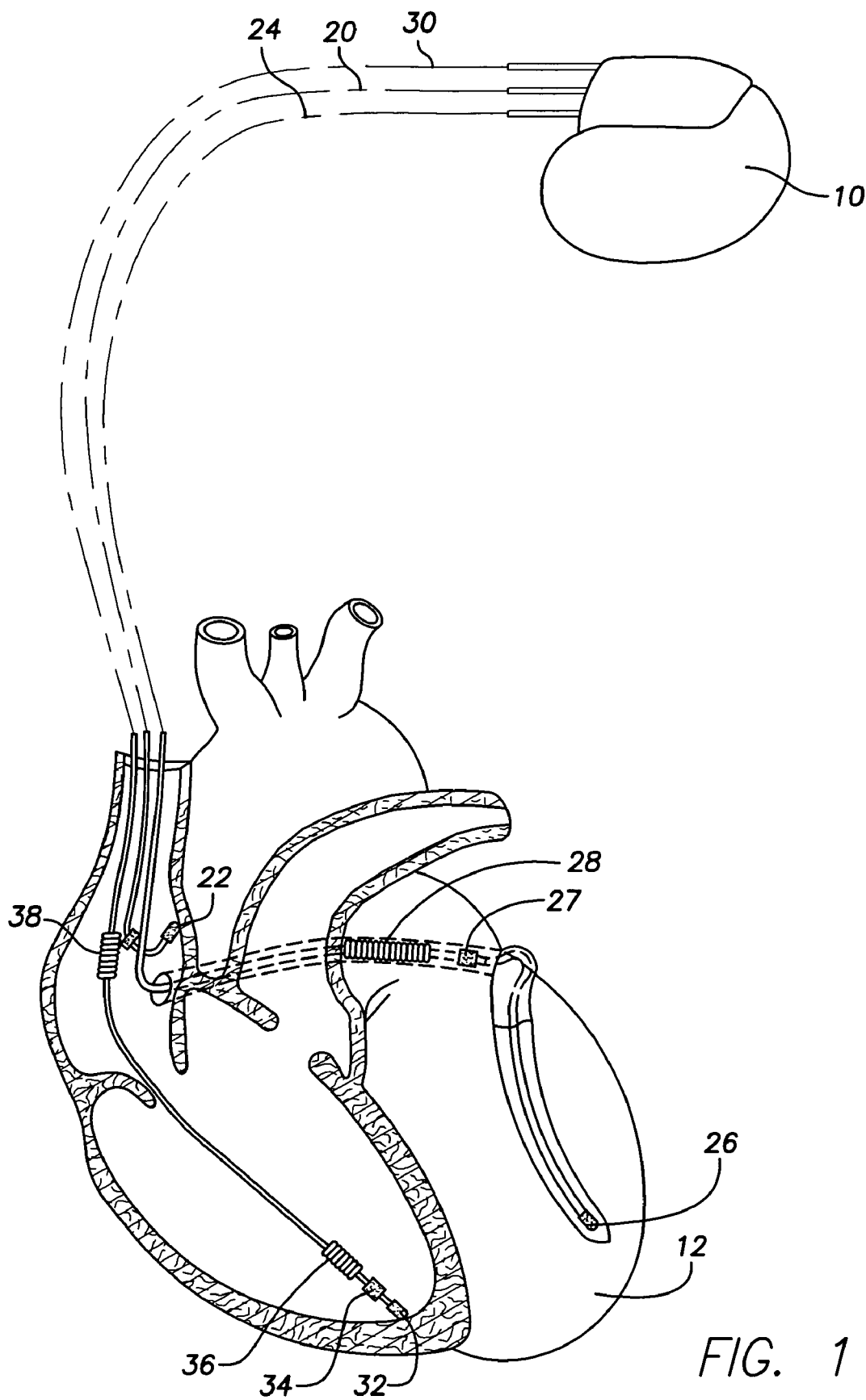
FIG. 1 shows an implantable cardiac stimulation device in contact with a patient's heart via a plurality of leads and electrodes.

As shown in FIG. 1, there is an implantable stimulation device 10, referred to hereafter as "device 10" for brevity, in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
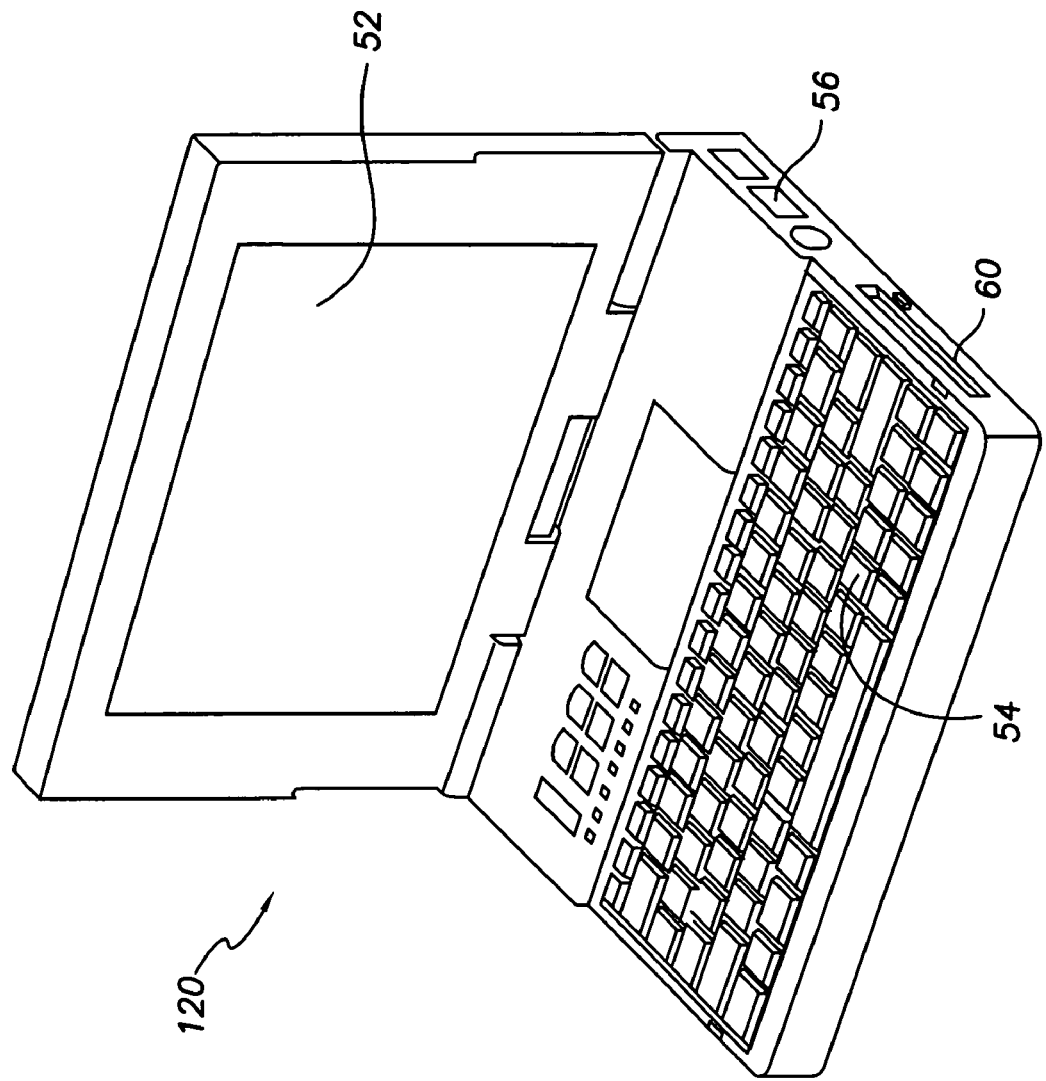
FIG. 2 shows a physician's programmer that can establish telemetric communication with the implantable device of FIG. 1.

FIG. 2 illustrates one embodiment of a physician programmer 50 that comprises a display 52. The programmer 50 can establish telemetric communication with the device 10 and the display 52 can present alphanumeric and graphical information relating to patient condition, implantable device performance and status, current programming, etc. to a user. The display 52 can comprise a liquid-crystal display (LCD), plasma display, array of light-emitting diodes (LEDs), or other display means capable of visually presenting information to a user. In one embodiment, the display 52 also includes touchscreen capability to allow a user to provide control inputs to the programmer 50.

In the embodiment shown in FIG. 2, the programmer 50 also comprises an input device 54, a connector 56, and a removable storage device 60. The input device 54 enables a user to input information and to select among various operational controls of the device 10. The input device 54 of the embodiment shown in FIG. 2 comprises a keyboard and a plurality of special function keys, however, in other embodiments, the input device 54 can further comprise a keyswitch matrix, microphone and corresponding speech recognition software, and/or can be embodied as touchscreen aspect of the display 52 as previously mentioned.

The connector 56 is adapted to physically and electrically mate with a connector of a telemetry wand so as to be removably connectable to the programmer 50. In certain applications, the telemetry wand facilitates telemetric communication between the device 10 and the programmer 50 in a well understood manner. The removable storage device 60 provides the capability of storing data on a removable media in a non-volatile manner. The removable storage device 60 in the embodiment shown in FIG. 2 comprises a removable disk, however, in other embodiments the removable storage device 60 can alternatively or in addition comprise a non-volatile solid state storage system, such as a flash memory system or an optical storage system, such as a writeable optical disc.

Figure 3:
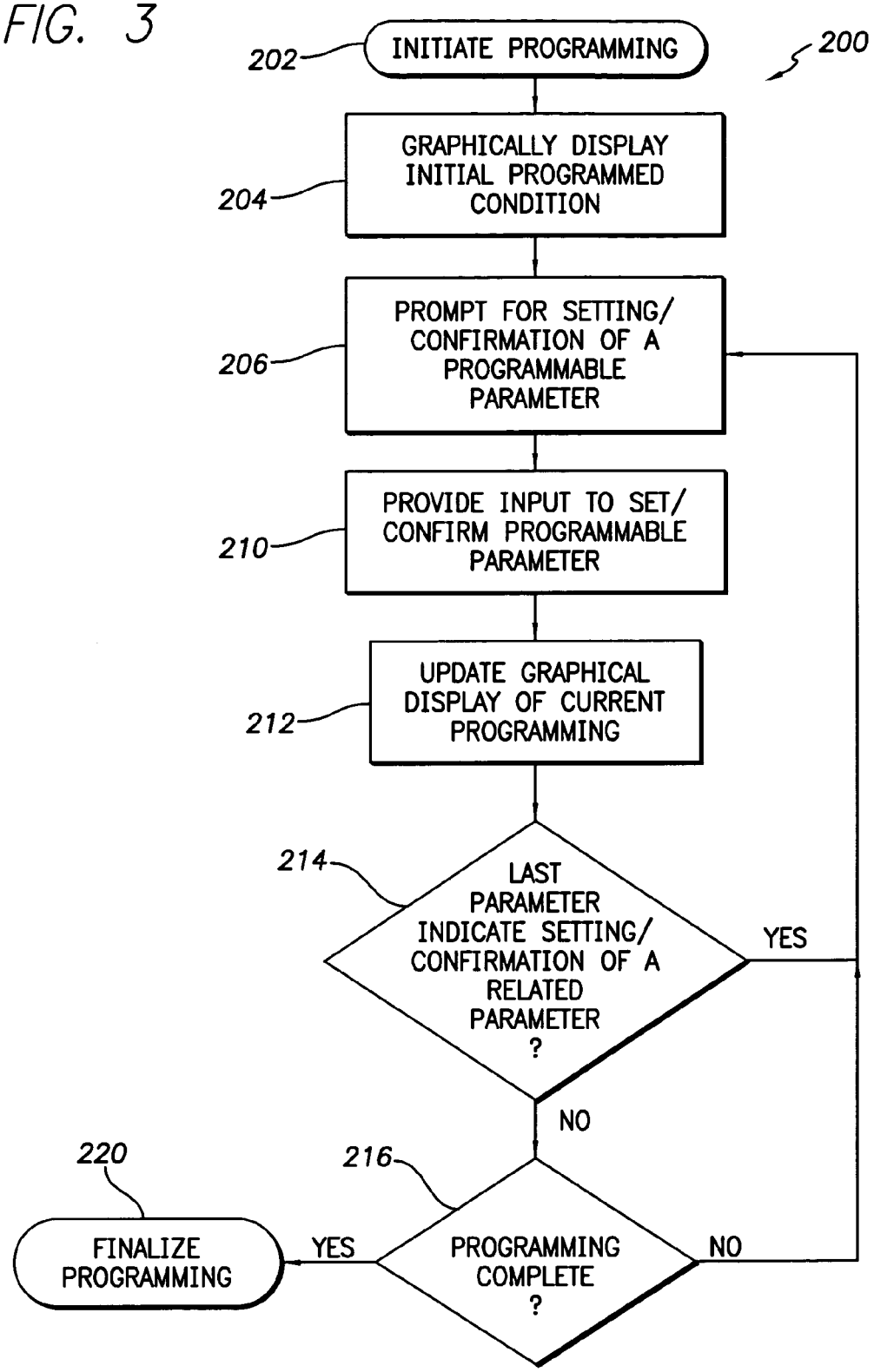
FIG. 3 is a flow chart illustrating embodiments of a method of displaying and programming parameters of an implantable device.

FIG. 3 is a flow chart of embodiments of methods of graphically programming parameters 200 of the device 10. State 202 indicates a start state where programming of the device 10 is initiated. State 202 indicates that the device 10 is in telemetric communication with the programmer 50 such that information relating to the condition and operation of the device 10 can be displayed via the display 52 and control inputs can be provided by the input device 54 for communication to the device 10. State 202 can indicate either initial programming at implantation or any of subsequent follow-up sessions where the operation and status of the device 10 is analyzed and/or modified.

In this embodiment, the display 52 of the programmer 50 graphically portrays a current programming state and expected cardiac activity under monitoring and treatment via the device 10 with the given set of programming in state 204. In one embodiment (FIG. 4), the display 52 illustrates a waveform indicative of the expected cardiac activity similar to the familiar ECG/IEGM waveform. The waveform graphically illustrates the temporal and relative magnitude of the expected cardiac activity of the four chambers in a single well-understood and familiar format.

In this embodiment, the waveform also comprises select-and-draggable embodiments of the input device 54 embodied within the display 52. In this embodiment, the waveform simultaneously portrays the expected influence of a plurality of different programmable parameters that may be modified via manipulation of the displayed waveform. Thus, the waveform graphically illustrates how a particular setting of a parameter or changes thereto would be expected to affect the duration, relative timing, etc. of a particular aspect of the cardiac activity in a manner very similar to a commonly used clinical diagnostic tool (ECG/IEGM waveforms).

A prompt is provided for a user to indicate one or more programmable parameters at a time that either need(s) to be set or have an existent value confirmed in state 206. In certain embodiments, the prompt of state 206 is provided by providing a distinctive color, brightness, and/or line pattern of the waveform corresponding to a programmable parameter. In other embodiments, the prompt is provided by indicating an icon, such as a square, circle, and/or mnemonic symbol or code to indicate the programmable parameter at an appropriate region of the waveform.

In certain embodiments, wherein the display 52 includes touchscreen functionality as part of the input device 54, the waveform can be manipulated by touching appropriate portions of the displayed waveform and directly manipulating the waveform as shown on the display 52 to provide control inputs to set/confirm a programmable parameter in state 210. In other embodiments, the waveform can be manipulated in a known graphical user interface (GUI) manner via selection of a desired portion of the displayed waveform with a movable mouse pointer and manipulated with a click-and-drag operation to the desired configuration to set/confirm a programmable parameter in state 210.

Figure 4:
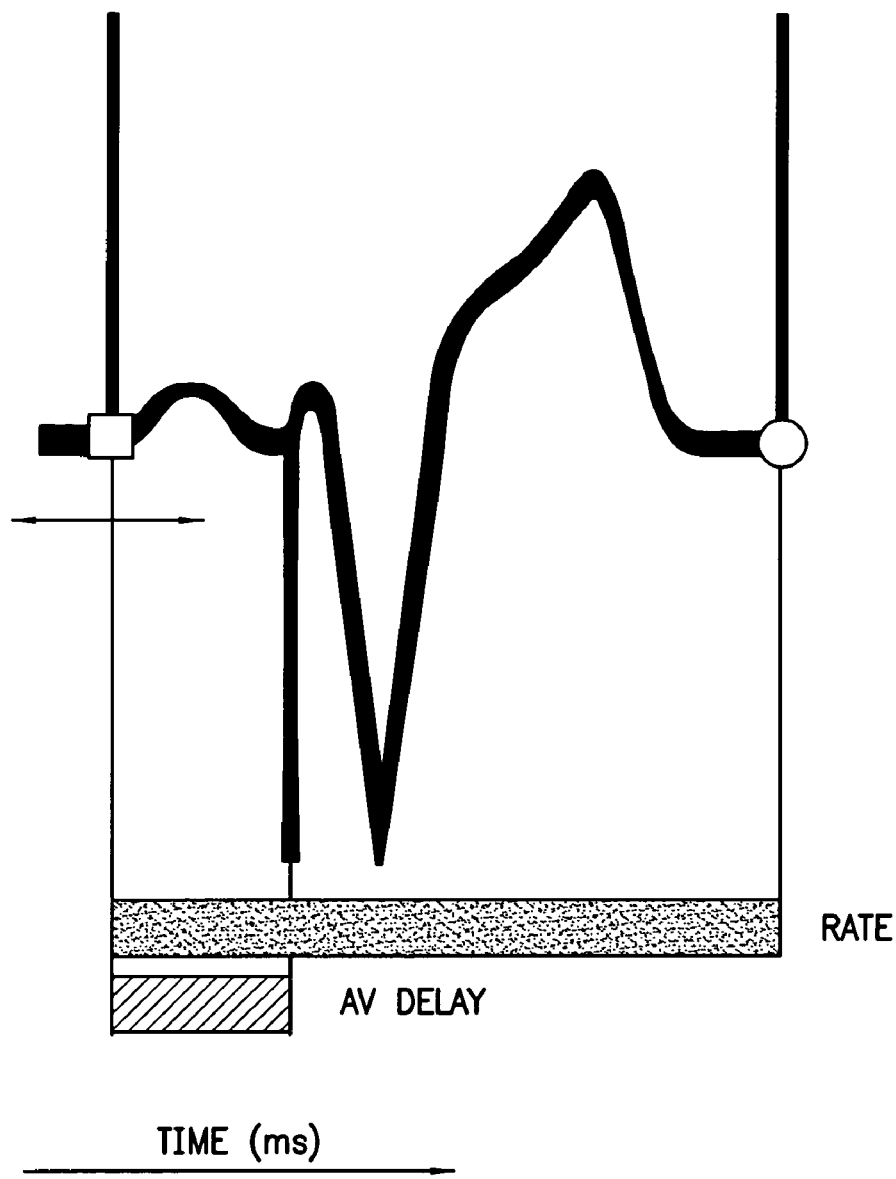
FIG. 4 is a sample wave form showing a cycle of a PQRST complex of a cardiac cycle with portions of the wave form comprising a user-selectable graphical user interface.

In one particular embodiment as shown in FIG. 4, the waveform includes a fixed point at the end of a schematic PQRST waveform depicted by the open circle. The waveform also comprises an adjustable or controllable portion indicated in this illustration by the open square and the bidirectionally-extending arrow positioned below the square. In this embodiment, a user can select an adjustable portion of the waveform (illustrated in this embodiment by the square) and move the position of the point of the waveform on the display 52 of the programmer 50 to affect changes in the programming of the implantable stimulation device 10 in state 210.

In this embodiment, manipulation of the user input 54 comprises manipulating the square left and right on the display 52 of the programmer 50. This changes the width of the complete waveform cycle which is portrayed in units of amplitude versus time. Thus, shortening or lengthening the width of the waveform changes the period of the cycle of the illustrated physiological process. In this embodiment, this changes the base rate parameter of the implantable device 10 comprising a pacemaker. The waveform displayed changes to indicate changes in the device 10 programming in state 212. This graphical depiction of the programming of the device 10 provides a user friendly manner of evaluating the expected operation of the device 10 in a format (electrogram waveform) that is familiar and intuitive to attending medical personnel.

It will be appreciated that changing and subsequently programming of certain parameters, such as the base rate, is subject to minimum and maximum values and that changes in the base rate may affect other parameters of the implantable device 10. In particular, an individual patient's particular physical condition would typically be evaluated by an attending clinician and the base rate, although programmable, would not generally be programmable below an indicated minimum rate, such as for example, 60 ppm.

It will also be understood that changes in certain parameters, such as the base rate, may affect other parameters such as an AV delay. This is evaluated in state 214 where a decision is made whether the last parameter set/confirmed affects other programmable parameters. In one particular example, a base rate setting of 90 ppm would indicate an AV delay that must be less than 300 milliseconds. According to one aspect of the invention, change of the base rate to a setting of 90 ppm in state 210 would result in a positive decision of state 214 and would automatically return to state 206 to change the AV delay to a period that is less than 300 milliseconds. A prompt would be provided in state 206 to indicate the affected parameter (AV delay in this example). As previously described, the user then has the option to set the new parameter (AV delay) to a desired value or to confirm the automatic setting in state 210.

It will also be appreciated that changes in one parameter, such as the base rate, can affect programmed values of multiple other parameters, such as for example, the PV delay, refractory period, etc. Thus, state 214 can return multiple positive decisions for a single set/confirmed underlying parameter and the loop of prompt, input, and waveform update of states 206, 210, and 212 can be repeated multiple times. It will also be appreciated that while the user-changeable waveform display illustrated in FIG. 4 indicates change along a horizontal scale, e.g., the time scale, other aspects of the invention include changing other parameters illustrated in this figure such as amplitude values, e.g., along a vertical scale.

If the decision of state 214 is negative, a decision is made in state 216 whether the complete set of programmable parameters has been set/confirmed. If further programming is indicated, the cycle of prompt, input, and waveform update of sates 206, 210, and 212 is repeated until state 216 indicates that user programming has been done. In one embodiment, state 216 determines not only that a user has set/confirmed all indicated programming, but also that the programming is satisfactory. For example, an affirmative result of state 216 can indicate that there are no conflicting or out of range programmed parameters. The evaluation of the satisfactory status of individual programmed parameters can occur when all needed parameters have been set/confirmed or can occur on an ongoing basis throughout the programming process. Once state 216 is affirmative, programming is finalized in state 220. In one embodiment, the finalization of state 220 includes transfer of the programming instructions from a temporary or batch programming memory to the operational memory of the device 10.

Figure 5:
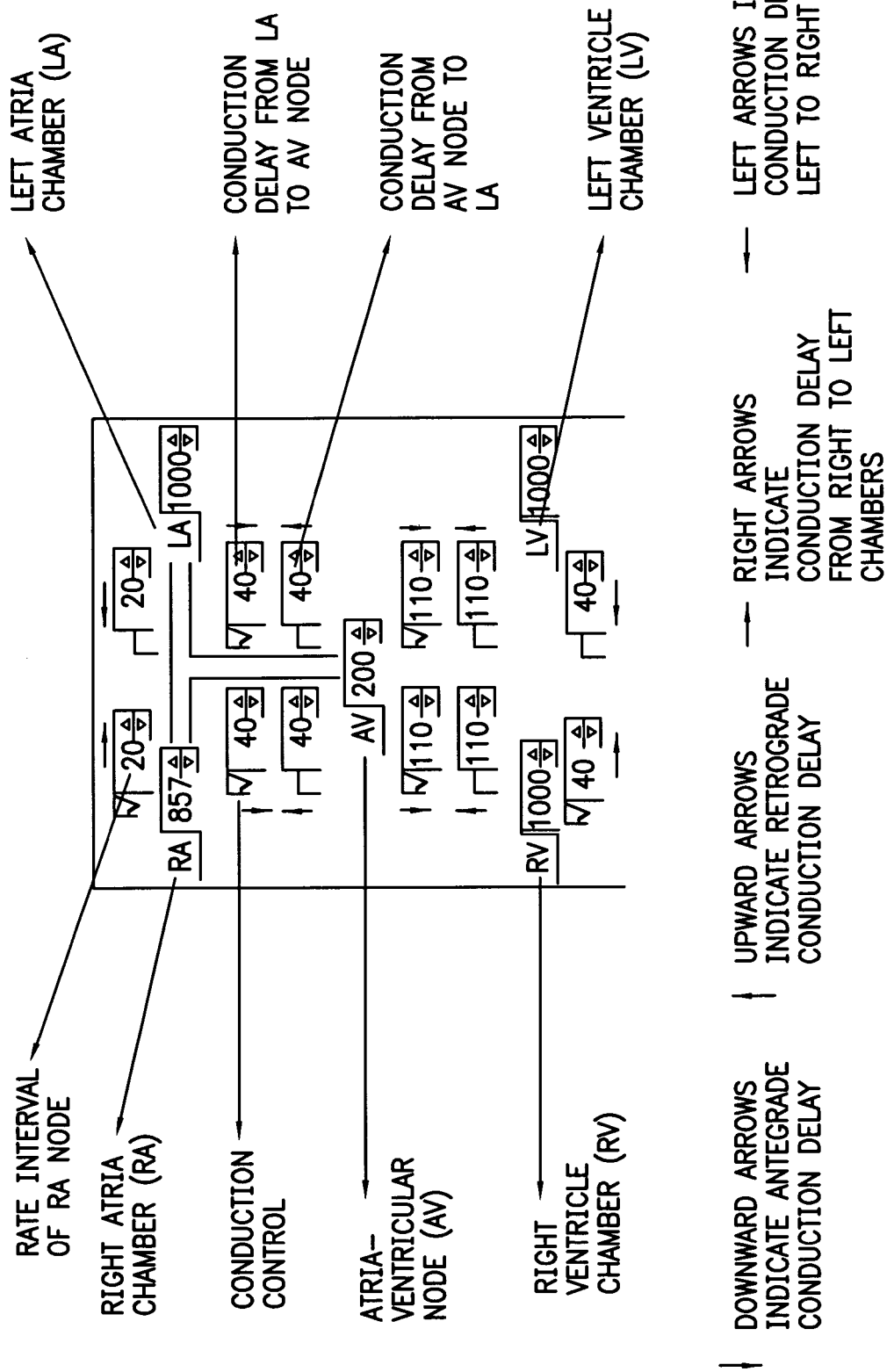
FIG. 5 is a sample control input screen showing a plurality of user-selectable and interrelated cardiac timing parameters for, in this embodiment, a four chamber cardiac stimulation device.

FIG. 5 illustrates a further embodiment of the invention showing details of the programmer display 52 including a graphical display of the programming parameters in a 2 dimensional spatial relationship. The display 52 shows multiple parameters arranged in a left-right and up-down spatial relationship corresponding generally to the relative spatial locations of the heart that would be expected to be affected by the particular parameters. For example, active downward arrows arranged on the left side of the display (corresponding to the right side of a supine patient as viewed by a clinician observer) indicate that the device 10 would be programmed for anterograde conduction in the right chambers, e.g. from the right atrium to the right ventricle. Upward directed active arrows would indicate retrograde conduction in these chambers.

Similarly, an active rightward directed arrow at the lower edge of the display 52 indicates a conduction delay from the right ventricle to the left ventricle. Further, in the embodiment illustrated in FIG. 5, a numerical value window indicates that the conduction delay is programmed at 40 ms. The embodiment illustrated in FIG. 5 includes parameters for all four chambers as well as the atria-ventricular node (AV). It will be appreciated that in specific applications the full functionality illustrated may not be indicated or used with a particular patient. In such applications, unused or unneeded parameters or interrelationships therebetween may not be show, may be dimmed or provided with null settings, or may be fully illustrated, but non-functional.

The graphical illustration of programming parameters of the embodiment show by FIG. 5 provides the advantage that an intuitive spatial relationship is visually provided between the particular parameters as graphically illustrated by the programmer 50 that corresponds to the spatial relationship of the respective chambers/regions of the patient's heart 12 that would be expected to be affected by the parameters. For example, the graphical display of the active right to left arrow arranged between and below the windows for the RV and LV corresponds to the spatial location of the RV and LV located at the lower end of the patient's heart and spaced towards the patient's right and left sides respectively. The rightward pointing arrow corresponds to the expected propagation of the cardiac depolarization from the RV to the LV and with a programmed conduction delay of 40 ms. Thus, a clinician can look at the lower left region of the display 52 and can readily intuit that the parameters shown there correspond to parameters expected to affect the activity in the observed lower left (patient's right) region of the patient's heart, e.g. the right ventricle.

The graphical illustration of programming parameters of the embodiment shown by FIG. 5 can occur either in combination or as an alternative to the embodiment of FIG. 4. For example, in one embodiment the graphical presentation of FIG. 5 is presented in state 210 upon selection of indicated portions of the waveform of FIG. 4 in response to a selection in state 206. In another embodiment, the graphical presentation of FIG. 5 is displayed in state 204 without necessarily the waveform of FIG. 4. In certain other embodiments, the device 10 automatically determines when and which electrodes are connected, such as via an impedance measurement, and thus automatically determines that programming for connected electrodes/chambers is indicated. Thus, the various parameter fields (RA, RV, RV-LV anterograde or retrograde conduction and delay, etc.) are automatically presented or activated when the device 10 determines that the appropriate corresponding electrode(s) is/are connected.

As previously mentioned, downwardly directed arrows indicate anterograde conduction delay, upwardly pointing arrows indicate retrograde conduction delay, right indicating arrows indicate conduction delay from right to left chambers, and left indicating arrows indicate conduction delays from left to right chambers. FIG. 5 also illustrates provision on the display 52 and the programmer 50 to discretely increment or decrement particular parameters, such as for example, the rate interval of the right atrial node which in the illustrated embodiment is selected and set at a value of 20 milliseconds. In other embodiments, a user can directly enter numerical values into parameters fields. The direct entry of parameter values can be provided in combination or as an alternative to incrementing/decrementing a given value.

Figure 6:
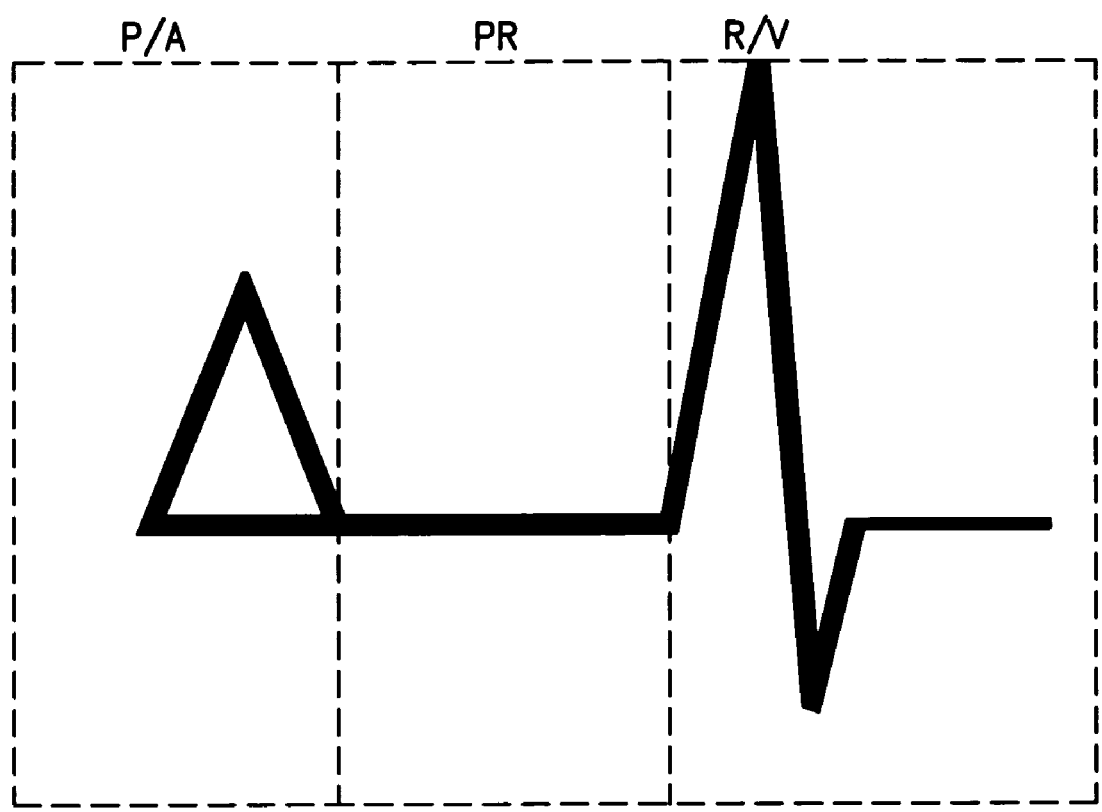
FIG. 6 is an initial programming screen with a schematic ECG.

FIG. 6 illustrates an initial programming screen with a schematic ECG waveform indicating a rough, initial programmed condition and indicating generally P- and R-waves of state 204. FIG. 7 illustrates details of the waveform of FIG. 6 that would be portrayed upon selection of various selected portions of the waveform of FIG. 6 in state 206 and, in particular, FIG. 7 illustrates selection of the P-wave region of the waveform of the schematic ECG of FIG. 6.

In this embodiment, the programmer 50 in communication with the device 10 automatically determines the electrodes connected to the device 10 and when a user selects, in this example, the P-wave region of the waveform in state 206, a schematic appears with all pertinent programmable parameters. This may include default settings, such as for example, simultaneous stimulation of both atria. Illustrated programmable parameters shown in FIG. 7 include voltage and pulse duration of the output to the right atrial lead, right atrial sensitivity, PVARP for the right atrial lead, output polarity, and sensing polarity. Similarly, a voltage and pulse duration of the output to the left atrial lead, left atrial sensitivity, PVARP for the left atrial lead, and output polarity and sensing polarity for the left atrial lead are also indicated.

In this example, the default for the relative timing of sensing of the atria, $A_R$ $A_L$, is zero milliseconds, e.g. simultaneous. A positive value for this parameter indicates sensing of the right atrium before the left atrium, and correspondingly a negative value indicates sensing of the left before the right with units measured in milliseconds. $P_R$ $A_L$ indicates a coupling interval if sensing in the right atrium occurs first and correspondingly $P_L$ $A_R$ indicates the coupling interval if sensing the left atrium occurs first.

FIGS. 8A-8D indicate several exemplary details of the waveform based on final settings with the schematic consistent with the programmed settings of states 210, 212. FIG. 8A indicates a waveform corresponding to a programmed setting of $A_R$ $A_L$ of positive 25 milliseconds or sensing the right atrium followed by sensing the left atrium 25 ms later. FIG. 8B indicates a portion of a waveform corresponding to a programmed setting of $A_R$ $A_L$ of minus 25 milliseconds or sensing the left atrium 25 ms before the right. FIG. 8C indicates a waveform corresponding to a programmed setting of $P_R$ $A_L$ of 50 milliseconds or pacing to the right atrium followed by sensing the left atrium 50 ms later. FIG. 8D indicates programmed settings and a corresponding waveform for $P_L A_R$ set at 0 milliseconds or substantially simultaneous pacing to the left atrium and sensing the right.

The specific parameters that need to be programmed and their particular programmed values will vary depending on the particular device 10 implanted, the electrodes implanted and to which chambers, and the particular physiological condition of the particular patient. Selection and setting of these parameters will be understood by a skilled clinician, however FIG. 9 is provided as one example of a set of programmable parameters and their settings for one particular application of an implantable device for one patient that are adaptable to the embodiments described herein.

Yet another aspect of the invention is a user-friendly, self-guiding and correcting aspect of the various programmable parameters of the device 10. Examples of these aspects will be described with respect to the embodiment of the implantable device 10 comprising an implantable cardiac stimulation device 10 and with programmable parameters relating to the monitoring and therapy provided by the device 10 with reference to FIG. 6. As previously described, one default programmed parameter for the device 10 can be that atrial stimuli are delivered simultaneously to both the atrium and the ventricle (AV pacing). However, it will be appreciated that this default may be changed depending on how the atrial and ventricular channels are programmed.

For example, in this embodiment, if the "PR" region of the schematic is selected before both the atrial and the ventricular parameters are programmed, a message would be provided instructing the user to first program both the atrial and ventricular channels before programming a PR interval. Once this is done, a user would be provided with the option to select among the available AV delay options. In the case that for the final programmed settings, $A_R$ precedes $A_L$, all timing for pacing to the atria start with the first stimulus, in this case the right atrial stimulus. The coupling intervals to the right ventricle and left ventricle may vary. The programmable option is the interval from the first atrial stimulus to the first ventricular stimulus.

Similarly, if sensing occurs first on one atrial channel, the sensed or PV interval will be from the first sensed atrial complex to the first ventricular-paced complex. Given the multiple variables, there may be interlocks (state 216) such that the paced and sensed AV delays cannot be programmed so as to conflict with coupling intervals programmed with respect to intra-atrial pacing/sensing and intra-ventricular pacing/sensing. It will also be appreciated that due to limitations in the sensing capabilities of the device 10, sensing times and intervals occur from when the device senses the signals, not necessarily from the actual leading or trailing edge of the physiological signal.

Although the preferred embodiments of the present invention have been shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A method of programming an implantable therapeutic stimulation device that senses from and delivers therapeutic stimulation to multiple sites within a patient under a plurality of individually programmable parameters, the method comprising:
    displaying a waveform, comprising:
    displaying a waveform indicating expected physiological activity under a first set of programmed parameters of the device;
    automatically determining which of the parameters need to be individually programmed;
    indicating the parameters that need to be programmed via indicating regions of the displayed waveform that are affected by the indicated parameter;
    providing control inputs to reprogram the indicated parameters; and
    indicating as indicated parameters are reprogrammed by modifying the waveform in accordance with the reprogrammed parameters; and
    graphically displaying the parameters that need to be programmed, comprising:
    graphically displaying the parameters in a spatial relationship corresponding to a spatial relationship of the sites within the patient expected to be affected by the parameters;
    providing control inputs to program the parameters; and
    indicating as parameters are programmed;
    wherein graphically displaying the parameters comprises displaying multiple parameters arranged in a left-right and up-down spatial relations corresponding to relative spatial locations of a heart.

2. The method of claim 1, wherein providing control inputs to reprogram the indicated parameters comprises temporarily programming the parameters and further comprising:
    automatically evaluating the temporarily programmed parameters entered; and
    if errors exist in the temporary programming, indicating the errors and awaiting corrective input, else programming the implantable device with the temporary programming.

3. The method of claim 1, wherein providing control inputs to reprogram the indicated parameters comprises manipulating a corresponding region of the displayed waveform.

4. The method of claim 3, wherein displaying the waveform comprises displaying the waveform as a graphical user interface and manipulating the corresponding region of the waveform comprises selecting and dragging the corresponding region of the waveform.

5. The method of claim 1, wherein providing control inputs comprises selecting a numerical parameter value.

6. The method of claim 5, wherein selecting a numerical parameter value comprises incrementing or decrementing the parameter.

7. The method of claim 1, wherein providing control inputs to reprogram certain of the indicated parameters that affect other programmable parameters automatically prompts for reprogramming the other affected parameters.

8. The method of claim 1, wherein the programmed parameters comprise AV delay.

9. The method of claim 1, further comprising automatically determining which of a plurality of sensing and stimulation electrodes are connected to the device.

10. The method of claim 1 wherein graphically displaying the parameters further comprises arranging active downward arrows on a left side of the display to correspond to a right side of a supine patient as viewed by an observer indicating that the device is programmed for anterograde conduction in the right chambers.

11. The method of claim 1 wherein graphically displaying the parameters further comprises arranging active upward arrows on a left side of the display to correspond to a right side of a supine patient as viewed by an observer indicating that the device is programmed for retrograde conduction in the right chambers.

12. The method of claim 1 wherein graphically displaying the parameters further comprises arranging active rightward directed arrows at a lower edge of the display indicating a conduction delay from a right ventricle to a left ventricle.

13. The method of claim 12 further comprising displaying a numerical value window indicating a numerical value of the conduction delay.

14. The method of claim 1 wherein parameters for four chambers of the heart are graphically displayed, the graphic displaying comprising:
   arranging parameters on a top-left side of the display to correspond to a right atrial chamber of the heart;
   arranging parameters on a bottom-left side of the display to correspond to a right ventricular chamber of the heart;
   arranging parameters on a top-right side of the display to correspond to a left atrial chamber of the heart; and
   arranging parameters on a bottom-right side of the display to correspond to a left ventricular chamber of the heart.

15. A method of programming an implantable therapeutic stimulation device sensing from and delivering therapeutic stimulations to multiple sites within a patient under a plurality of individually programmable parameters, the method comprising:
   automatically determining which parameters need to be individually programmed;
   graphically displaying the parameters that need to be programmed such that the parameters are respectively displayed in a spatial relationship corresponding to a spatial relationship of the sites within the patient expected to be affected by the parameters;
   providing control inputs to program the parameters; and indicating as parameters are programmed;
   wherein graphically displaying the parameters comprises displaying multiple parameters arranged in a left-right and up-down spatial relations corresponding to relative spatial locations of a heart.

16. The method of claim 15 wherein providing control inputs temporarily programs the parameters and further comprising:
   automatically evaluating the temporarily programmed parameters; and
   if errors exist in the temporary programming, indicating the errors and awaiting corrective input, else programming the implantable device with the temporary programming.

17. The method of claim 16, wherein evaluating the temporarily programmed parameters occurs once all of the needed programming is entered.

18. The method of claim 15, further comprising displaying a waveform indicating expected physiological activity under a current set of the programmed parameters.

19. The method of claim 15, wherein the programmable parameters comprise anterograde or retrograde conduction between two cardiac chambers.

20. The method of claim 15, further comprising automatically determining a number of sensing and stimulation electrodes connected to the device.

21. The method of claim 15 wherein graphically displaying the parameters further comprises arranging active downward arrows on a left side of the display to correspond to a right side of a supine patient as viewed by an observer indicating that the device is programmed for anterograde conduction in the right chambers.

22. The method of claim 15 wherein graphically displaying the parameters further comprises arranging active upward arrows on a left side of the display to correspond to a right side of a supine patient as viewed by an observer indicating that the device is programmed for retrograde conduction in the right chambers.

23. The method of claim 15 wherein graphically displaying the parameters further comprises arranging active rightward directed arrows at a lower edge of the display indicating a conduction delay from a right ventricle to a left ventricle.

24. The method of claim 23 further comprising displaying a numerical value window indicating a numerical value of the conduction delay.

25. The method of claim 15 wherein parameters for four chambers of the heart are graphically displayed, the graphic displaying comprising:
   arranging parameters on a top-left side of the display to correspond to a right atrial chamber of the heart;
   arranging parameters on a bottom-left side of the display to correspond to a right ventricular chamber of the heart;
   arranging parameters on a top-right side of the display to correspond to a left atrial chamber of the heart; and
   arranging parameters on a bottom-right side of the display to correspond to a left ventricular chamber of the heart.

* * * * *